United States Patent [19]

Chance et al.

[11] 4,162,405
[45] Jul. 24, 1979

[54] FLYING SPOT FLUORO-METER FOR OXIDIZED FLAVOPROTEIN AND REDUCED PYRIDINE NUCLEOTIDE

[76] Inventors: Britton Chance; John R. Sorge, both c/o Johnson Research Foundation, University of Pennsylvania, Philadelphia, Pa. 19174

[21] Appl. No.: 908,794
[22] Filed: May 23, 1978
[51] Int. Cl.$^2$ ............................................. G01N 21/38
[52] U.S. Cl. ................................... 250/461 B; 424/7
[58] Field of Search ............... 250/461 B, 461 R, 458, 250/459; 424/2, 7

[56] References Cited
U.S. PATENT DOCUMENTS

| 3,449,571 | 6/1969 | Hoerman ..................... 250/461 B X |
| 3,657,537 | 4/1972 | Wheeless, Jr. et al. .......... 250/461 B |
| 3,770,349 | 11/1973 | Legorreta-Sanchez ..... 250/461 B X |

Primary Examiner—Davis L. Willis
Attorney, Agent, or Firm—Herman L. Gordon

[57] ABSTRACT

A method and apparatus for measuring the heterogeneity of oxygen delivery to perfused and in situ organs. A laser is employed as a flying spot scanning excitation fluorometer source which provides excitation for either oxidized flavoprotein of the mitochondrial space or reduced nucleotide of mitochondrial and cytosolic spaces. Emission from the two fluorochromes is acquired at $10^4$ to $10^5$ data points per sec. and histograms of the fluorescence intensity versus the number of occurrences of that intensity are displayed. The histograms show alterations of the intensity and the degree of heterogeneity of the redox states of the organ tissue under study.

18 Claims, 8 Drawing Figures

FLYING SPOT FLUORO-METER FOR OXIDIZED FLAVOPROTEIN AND REDUCED PYRIDINE NUCLEOTIDE

FIELD OF THE INVENTION

This invention relates to spectrofluorometers, and more particularly to a spectrofluorometer system employing flying spot excitation for deriving data in connection with oxygen delivery to perfused and in situ organs.

BACKGROUND OF THE INVENTION

The perfection of surface fluorometry for measuring local metabolic states and for discerning the profiles of hypoxic regions has won considerably greater acceptance in perfused models, where the precision is high and the possibilities of artifacts few, and in situ organs, where care is required lest blood flow and blood volume changes in the area of the recording give spurious readings. In the latter case, satisfactory readout of reflectance signals at appropriate wavelengths, together with algorithms for applying a correction factor, lead to a remarkable clarity of recording, in spite of large hemodynamic changes. In particular, the instruments have been designed to record at a single point, or, more accurately, in an area from 10 microns to several millimeters in diameter. While this has been eminently satisfactory for giving a report on the general state of the area under observation, particularly in response to ischemia and hypoxia, the combined technique of freeze-trapping and low temperature scanning has suggested a considerable heterogeneity of the redox states of the brain cortex, heart, and liver, indicating microheterogeneity of the metabolic activity and/or of oxygen delivery to various parts of the organ. While the low temperature scanning procedure gives a "stop motion" picture of the phenomenon with considerable accuracy and resolution and the possibility of three-dimensional reconstruction, there is a need to be able to carry out on-line studies of distributions of redox states in a given area involved, for example, in a localized hypoxia in heart or brain. The goals may be either to identify an appropriate heterogeneous state for freeze-trapping and further examination of "maximal deviation" metabolic state, or to read off as a function of time the effects on the size of a hypoxic region in a normoxic tissue of such parameters as oxygen tension substrates, inhibitors or pharmacologic reagents.

Two approaches to a two-dimensional scan of tissue fluorescence have already been tried: first, the television approach with varying degrees of sophistication in the camera, i.e., image amplifiers, image converters, etc. Secondly, image amplifiers can be focussed on charge-coupled devices with considerable improvement in dynamic range, stability, etc. Preliminary tests of the latter configuration have been made. The performance of these techniques is not enhanced by the use of laser excitation of fluorescence, simply because the average power of a laser may not be very high, as compared with that of 1 KW Hg or Xenon (used with appropriate filters), when broadcase illumination over the sample is employed.

The flying spot scanner has previously been used with cathode ray tubes as light sources, and becomes advantageous for fluorescence excitation when a laser is used as the light source. For the past several years, cheap and efficient laser light sources have been available at wavelengths appropriate to oxidized flavoprotein and reduced pyridine nucleotide, and comparisons of the various lasers with mercury arcs, etc. have been made, particularly the He-Cd laser.

SUMMARY OF THE INVENTION

The present invention employs a flying spot fluorometer, affording a two-dimensional display and a signal histogram. A straight-forward example is the application of the instrument to liver, where heterogeneity of aerobic metabolism and homogeneity of anaerobic metabolism are clearly demonstrable. In perfused heart an on-line estimate of the surface area of a model infarct can be determined. In the brain, studies of changes of the distribution of hypoxic areas can be readily made, and are of great interest. This instrument can be used to effect the establishment of "maximum deviation metabolic states" at appropriate times following supplementation of perfused organs with substrates and inhibitors in normal and pathological states and thereby affording optimal material for detailed localized analytical biochemical procedures.

A simple and expedient approach can be chosen comprising flavoprotein excitation with the 422 nm line of the 10 mW He-Cd laser (Liconix Model 902). There can also be successfully used the Argon ion Laser (Lexel Model 96) emitting not only at 457.9 nm, suitable for flavoprotein, but also at 350/363 nm., suitable for excitation of reduced pyridine nucleotide.

The 1 mm spot of the He-Cd laser can be used directly as a source or via a lens and pinhole ($100\mu$). An appropriate lens can give a spot of about $50\mu$ or a diffraction-limited spot ($0.33\mu$). In studies of liver there have been used a spot size of 0.1 mm and a scan pattern of 2 cm on edge for small animal models (rat brain, liver, kidney and heart).

A suitable scan system for the desired applications of the present invention are preferably such as to provide a repetition frequency of from one every few seconds to several times a second. A typical practical set of scan frequencies, for example, would employ 200 Hz on one axis 1 Hz on the other, giving $4 \times 10^4$ data points, which would be adequate for many of the purposes intended for the system.

With scanning speeds of the order above mentioned, electromagnetic drive of front-surface mirrors appears to be simplest and most economical. Of the various types of scan, the rectangular scan is appropriate for the present purpose and is the simplest to generate, although in cases where in ischemic zone is at the center of the pattern, a spiral scan would be possible. Either of these can be obtained directly or by small modifications from the two-axis scanner. Usually a square pattern suffices, but when the shape of the figure in which the metabolism is to be studied is significantly different from that of a rectangular shape, various other scan shapes can be programmed. A spiral scan may ultimately prove most useful since it requires similar band widths for both X and Y scanners.

It has been found to be possible to compensate the NADH fluoresence signal from a variety of tissues, for example, brain, by subtracting from the fluorescence signal a reflectance signal from the same area. The flying spot system of the present invention utilizes such compensation by collecting the reflectance data from the same area at the same time as the fluorescence data, for example by using a beam splitter and a second photomultiplier with a filter transmitting only the excitation wavelength (350-363 nm in the case of the Argon ion laser or 442 nm in the case of flavoprotein signals using the He-Cd laser). The correction factor is applied in "real time" simply by subtracting the signals in the appropriate ratio and connecting the difference signal to the display and histogram channels.

Thus, the flying spot method provides all the possibilities for compensation for hemodynamic effects that have currently been available with the signal point method. It is possible that compensation with flying spot techniques may be more effective since the appropriate reflectance at an appropriate point is applied to the signal.

The distance between the two-axis scanner and the sample can be relatively large, i.e., one meter or the like, and with an appropriate telescope the signal acquisition can be similarly distant. Thus, the system of the present invention is suitable for intraoperative procedures; minimal interference would be involved, and with suitable illumination (red light) minimal interference with the scanner would be involved. Alternatively, the laser may be modulated at near 1 MHz to avoid room lignht interference. In this case a large dynamic range is required, which may be obtained by dynode voltage regulation.

On-line analysis of the data output is of great importance, and the system of the present invention therefore employs multichannel analysis and histogram display for this purpose. The goal of the multichannel analysis is to present histograms of the frequency of occurrence of signal intensities with a certain range.

Accordingly, a main object of the present invention is to provide a novel and improved method and apparatus for measuring and evaluating the oxygen delivery to perfused and in situ organs which overcomes the deficiencies and disadvantages of previous systems employed for this purpose.

A further object of the invention is to provide an improved flying spot fluorometer scanning systems which provides efficient excitation for either oxidized flavoprotein or reduced nucleotide and which provides a monitor display of fluorescence of the excitation area as well as a histogram display of the fluorescence intensity versus the number of occurrences of that intensity, thereby showing alterations of the intensity and the degree of heterogeneity of the redox states of the organ tissue under study.

A still further object of the invention is to provide an improved spectrofluorometer system employing laser flying spot excitation for deriving data in connection with oxygen delivery to perfused and in situ organs, providing accurate and reliable on-line data with respect to heterogeneity of distribution of redox states in an area under study, for example, in a localized hypoxia in heart, brain, liver, or other organ, facilitating identification of specific heterogeneous states, and enabling the reading off as a function of time the effects on the size of a hypoxic region in a normoxic tissue of such parameters as oxygen tension substrates, inhibitors or pharmacologic reagents.

BRIEF DESCRIPTION OF THE DRAWINGS

Further objects and advantages of the invention will become apparent from the following description and claims, and from the accompanying drawings, wherein:

DESCRIPTION OF A PREFERRED EMBODIMENT

Figure 1:
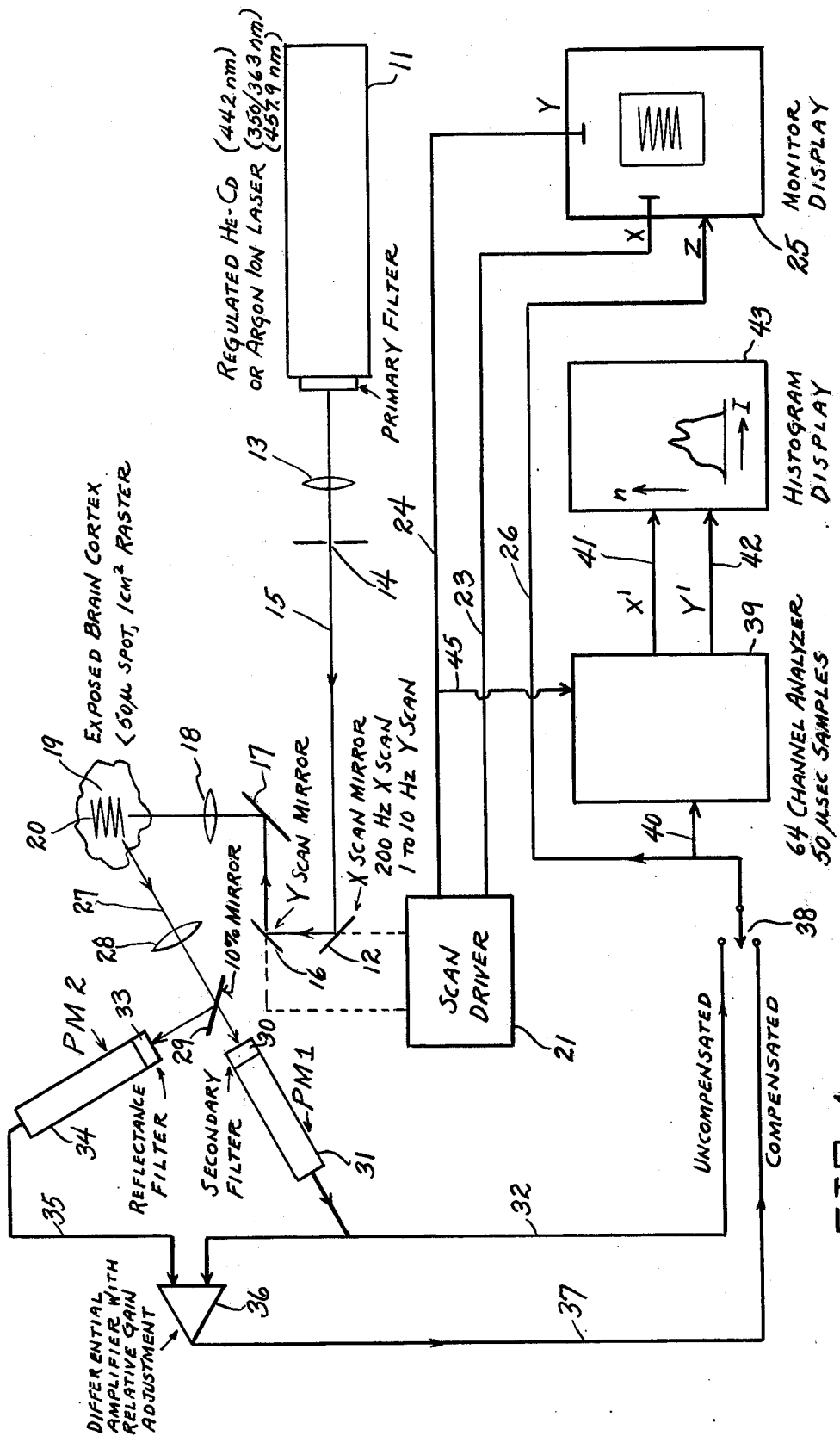
FIG. 1 is a block diagram of a laser flying spot 2-dimensional microfluorometer with on-line histogram display, in accordance with the present invention.
Figure 2:
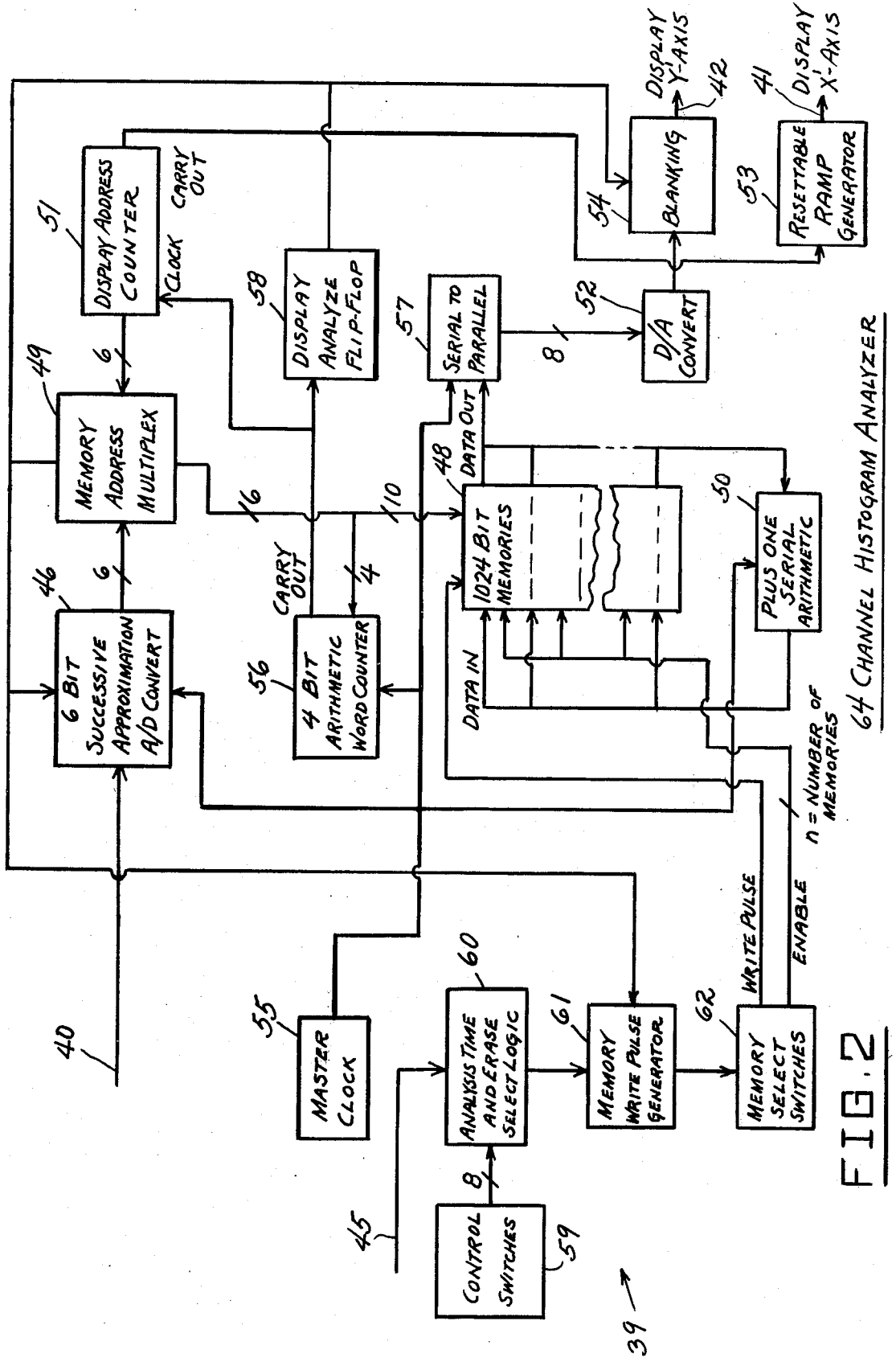
FIG. 2 is a block diagram of the 64-channel histogram analyzer employed in the microfluorometer of FIG. 1.

Referring to the drawings, FIG. 1 illustrates schematically a typical flying spot spectrofluorometer apparatus according to the present invention. The apparatus comprises a laser source 11, which may be a regulated He-Cd laser similar to Liconix Model 96, providing a 442 nm excitation beam, suitable for oxidized flavoprotein excitation, or an Argon ion laser similar to Lexel Model 96, providing not only a 457.9 nm beam suitable for oxidized flavoprotein but also emitting at 350/363 nm, suitable for excitation of reduced pyridine nucleotide. The laser source 11 is suitably mounted to direct its beam 15 toward a vibrating 45°-inclined front surface X-scan mirror 12. A suitable focussing lens 13 and pinhole 14 may be provided in the optical path of the laser beam. The pinhole 14 may be about 100 microns in diameter.

The beam 15 is reflected with X-directional sweep toward a vibrating 45°-inclined front surface Y-scan mirror 16, which reflects the beam, with superimposed Y-directional sweep, toward a fixed 45°-inclined plane mirror 17, which in turn reflects the composite-sweep raster beam through a focussing lens 18 to the tissue area 19 under study, thereby delivering the excitation raster 20 to said tissue. The tissue 19 may typically be exposed brain cortex, and the raster 20 may have a 0.1 mm spot size and may form a square scan pattern 2 cm on edge; this may be employed for small animal models, for example, for studies of rat brain, liver, kidney, heart, etc.

The X-scan mirror 12 and Y-scan mirror 16 are driven in a conventional manner by an electromagnetic drive mechanism 21, which also furnishes synchronized X-sweep voltage via a line 23 and synchronized Y-sweep voltage via a line 24 to the X and Y sweep terminals of a monitor display cathode ray tube assembly 25. The raster of the monitor assembly 25 is intensity-modulated by a modulation signal from a signal input line 26 connected to the Z-terminal of the monitor display device 25.

The fluorescence emission from the sample 19 is shown as a beam 27 (which may include reflected excitation light) and is focussed by a lens 28 onto a 45°- inclined beam splitter 29, which may comprise a conventional partly-silvered mirror. A portion of beam 27 passes through the beam splitter 29 and an emission wavelength filter 30 to a first photomultiplier tube 31, whose electrical output appears at a signal output line 32. The remaining portion of beam 27 is reflected from the beam splitter and passes through a reflectance filter 33 (passing only excitation wavelength light) to a second photomultiplier tube 34, whose electrical output appears at a signal output line 35. The lines 32 and 35 are connected to the inputs of a differential amplifier 36 whose output line 37 carries a reflectance-compensated signal, being the main signal of line 32 from which is substracted the reflectance signal of line 35. The uncompensated main signal from line 32 or the reflectance-compensated signal from line 37 may be selectively connected to the Z-input line 26 via a selector switch 38.

The Y-sweep synchronized signal from line 24 is connected as a sweep-synchronizing input via line 45 to a 64-channel Analyzer 39, and the Z signal from line 26 is connected to the emission analog signal input line 40 of said Analyzer 39. The Analyzer 39 has display output signal lines 41, 42 connected to a histogram visual display unit 43, which may comprise an oscilloscope.

With a Y-sweep frequency of 1 Hz and an X-sweep frequency of 200 Hz, giving $4 \times 10^4$ data points, and using a screen of medium-to-long persistence in unit 25, the Z-axis modulating signal in line 26 will provide an adequate 2-dimensional display (a $4 \times 10^4$ element picture) of the fluorescence developed by the excitation raster 20 over the tissue area 19 under study, without requiring other special storage techniques. With these scanning speeds, the electromagnetic scan driving unit 21 can be relatively simple and of economical construction. The reflectance compensation is quite effective since the appropriate reflectance subtraction signal can be applied for each flying spot scan point.

The on-line analysis of the data output is of great importance, and the multichannel Analyzer 39 and histogram display unit 43 are employed for this purpose. The function of Analyzer 39 and display device 43 is to present histograms of the frequency of occurrence of signal intensities with a certain range. The design of the unit 39 is straight-forward and centers around a 6-bit free-running analog-to-digital converter 46 which cylces once every 50 $\mu$sec. The differential amplifier output is applied via line 40 as the analog input to converter 46. The digital output of converter 46 is applied to the address inputs of a random access memory (RAM) 48 via a memory address multiplex unit 49. Samples are obtained at a 20 KHz rate, and a uniformly fluorescent raster surface 20 would yield 20,000 "counts" per second. This "worst case" suggests a 16-bit "channel" data word (65,535 counts). The random access memory 48 can contain 64 sixteen-bit data words (channels), and the 64 channels are provided with 1.6% (full scale) amplitude resolution.

In use, the Analyzer 39 is triggered on and off by a synchronization signal to the logic unit 60 from the Y-deflection drive circuit line 45, assuring that the analysis represents one or more integral scans. Every 50 $\mu$sec a count (+1) is added by an arithmetic unit 50 to the data channel addressed by the A/D converter unit 46. A 1 Hz Y-axis scan rate thus yields a histogram of the scanned area with a resolution of 20,000 points; a homogeneous surface would fill one of the 64 channels with 20,000 counts, whereas an ideally random heterogeneous surface would fill all channels equally with 312 counts.

The master clock 55 controls the conversion rate of A/D converter 46 and is the clock input to the arithmetic word counter 56 which provides addresses for the 16-bit data word in a serial fashion. The display address counter 51 advances sequentially after each data word cycle.

The histogram is generated (and made visible) by multiplexing (via unit 49) the output of a 6-bit binary counter 51, fed by a 4-bit arithmetic word counter 56, to the address ports in place of the A/D converter 46, sequentially addressing the data channels, and reading their contents, via a series-to-parallel unit 57 and a D/A converter 52. The counter circuit 51 activates a resettable ramp generator 53 to provide at line 41 the X' deflection signal for an oscilloscope in the histogram display unit 43, the D/A converter 52 providing the Y'-axis information at line 42 via a blanking unit 54, which is controlled by signals from multiplex unit 49 and a display analyzer flip-flop 58, in turn controlled by the carry-out signal of counter 56.

The service operating characteristics of the RAM unit 48 are adjusted in a conventional manner by means of a control switch unit 59 and intervening conventional memory control units 60, 61 and 62.

The range of the signal acquisition is adjusted by increasing the photomultiplier high voltage until the highest signal is just within the register of the Analyzer 39. Then the signals may be distributed over the 64 channels. In practice, it has been found that the intensity distributions for most organs cover only about one-third of the 64 channels, and offset of the signal may be used to spread it over more channels.

In the embodiment of FIG. 1, for example, an He-Cd laser at 442 nm will illuminate the two-axis mirror system from which the raster 20 is projected onto the tissue 19 through a suitable lens 18, giving a 0.05 to 0.3 mm spot and a 1 cm$^2$ raster. The light from raster 20 is picked up by the first photomultiplier tube 31 through the Fresnel lens 28, or alternatively, through a light guide, and by the compensating second photomultiplier tube 34, as above described. The output signal from the photomultiplier tube 31 may be fed directly (uncompensated) to the display oscilloscopes in one closure position of switch 38, or (compensated) the photomultiplier output signal in line 35 may be subtracted from that in line 32 by the differential amplifier 36 and the difference signal may be fed to the oscilloscopes via line 26, in the other closure position of switch 38.

In typical experiments employing the above-described apparatus, rat liver mitochondria were prepared and were suspended in mannitol (0.255 M), sucrose (0.075 M) and Tris-sulfate buffer (5 mM), pH=7.4. In State 2 no substrate was added.

Figure 3:
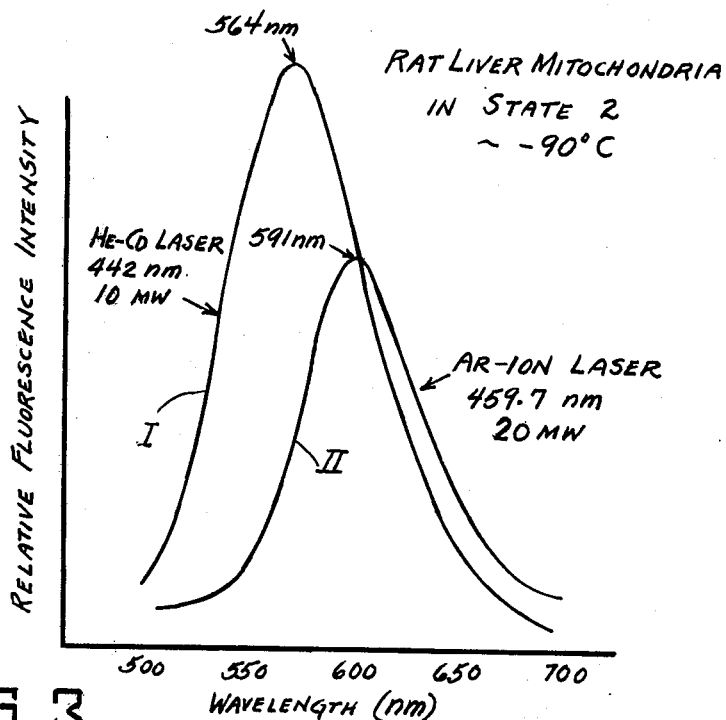
FIG. 3 illustrates monitor displays provided by the apparatus of FIG. 1, comprising emission spectra of rat liver mitochondria flavoprotein excited by the He-Cd laser at 442 nm with a Wratten 4 guard filter and by an Argon ion laser at 459.7 with a Wratten 12 guard filter.

The fluorescence emission from flavoprotein in response to the two laser wavelengths is indicated in FIG. 3. The Fp signal is identified with the pyruvate and $\alpha$-ketoglutarate dehydrogenases of mitochondrial matrix and flavoprotein fluorescence was expected in State 2 since flavoprotein fluoresces in the oxidized rather than the reduced form. Considering first excitation with the 10 mW He-Cd laser at 442 nm (trace I), a filter combination, plus the purity of the emission, permitting recording to begin at a wavelength of about 470 nm and to achieve a considerable intensity at 490 nm. The apparent peak of the emission band was at 564 nm.

Trace II of this Figure shows the emission of flavoprotein when excited at 459.7 nm with the 20 mW Aron ion laser. In this case, the incomplete suppression of other wavelengths required a guard filter which did not begin to transmit sufficiently until 510 nm, and the apparent peak of the emission spectrum was at 591 nm.

The perfused rat liver is of great interest for a variety of reasons. The first of these is the variety of its metabolic pathways and the susceptibility to changes of metabolic patterns depending upon the substrates, inhibitors, etc., in the perfusate. Secondly, it has been considered from a variety of standpoints to be functionally heterogeneous. Thirdly, low temperature redox ratio scanning has shown not only considerable heterogeneity but changes of heterogeneity induced by changes of metabolism, for example, with ethanol.

Figure 4:
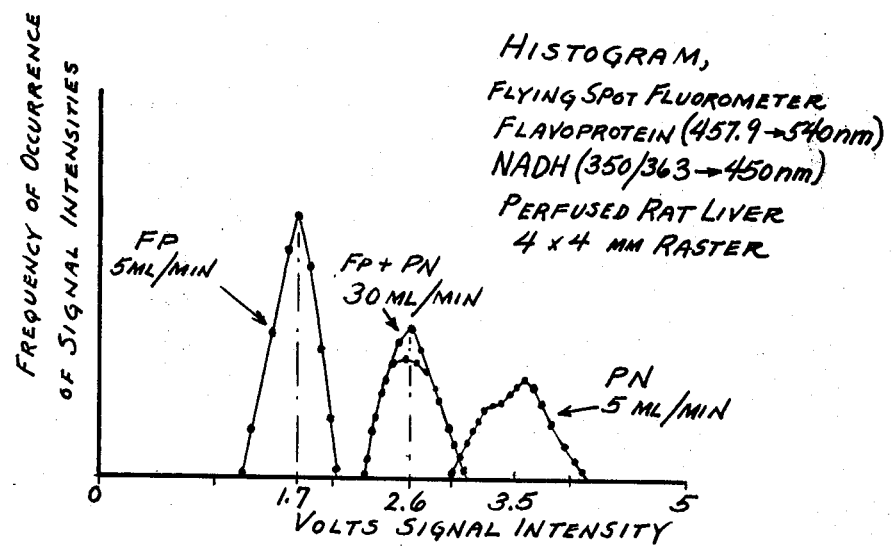
FIG. 4 illustrates enlarged histogram displays provided by the apparatus of FIG. 1, giving a comparison of responses of Fp (459.7 to 540 nm) to low flow hypoxia in perfused rat liver.

A diagram of the histogram display of the perfused liver is shown in FIG. 4. There are actually four histograms displayed in this Figure, two for Fp and two for PN. At a perfusion rate of 30 ml/sec the histograms for Fp and PN are superimposed. This is consistent with the origin of both pyridine nucleotide signal and Fp signal development from the mitochondria in which NADH and Fp are near equilibrium.

On establishing a hypoxia by decreasing the flow rate to 5 ml/sec, the two superimposed peaks separate; the Fp shifts to the left to a decreased intensity, and the NADH (FN) shifts to the right to a higher intensity. The full scale of the histogram is 5 volts output from the photomultiplier collector. Thus, the position of the midpoint of the two histograms at normal flow is at 2.6 volts while that of the flavoprotein at low flow is at 1.7 volts, and the NADH is at 3.5 volts, respectively a decrease of 37% and an increase of 42%. Single area fluorometric measurements with a 2 to 4 mm light guide give anoxic responses in liver, heart and brain in the same range. Under the higher flow conditions, the width of the histogram at its base for both Fp and PN is about 32% of its mean value. As the flow is decreased the width of the flavoprotein signal decreases to a value of about 29%. What is significant however is that the pyridine nucleotide histogram at the low flow appears to break up into two approximately equal populations, one at a signal voltage of 3.45 volts and the other at a signal voltage near 4.0 volts, while the flavoprotein signal appears to remain homogeneous.

The amplitudes of the Fp and PN signals suggest heterogeneity changes in the signals at low flow as compared with high flow. The amplitude of the Fp signal increases by 65% while that of the PN signal decreases (the average of the two peaks) to about 66%. In this case, the cytosolic component of the PN signal appears to have a different redox state from the mitochondrial component which is precisely indicated by the Fp signal.

Figure 5A:
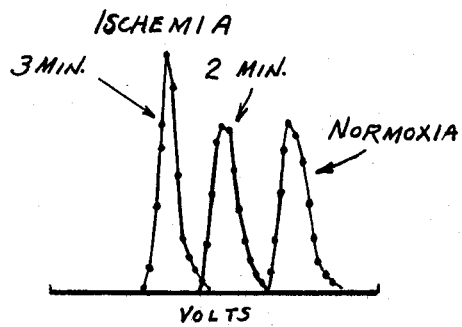
FIGS. 5A and 5B illustrate enlarged histograms displays obtained from the apparatus of FIG. 1 of flavoprotein fluorescence signals from perfused rat liver in normal, ischemic and recovered states, FIG. 5A being derived with Saran wrap covering the liver and FIG. 5B being derived with the liver uncovered.

The histograms shown in FIG. 5A were obtained from perfused rat liver set up at 23° C. and scanned with wavelengths appropriate to Fp, as in FIG. 4. In the experiment associated with FIG. 5A the liver was covered with a Saran wrap and the kinetics of the normoxic-anoxic change were recorded as the flow to the liver was decreased from 30 ml/min to 0 by a blockade of the output from perfusion. The normoxic histogram is similar to that of FIG. 4, showing a width of 31% at the base. Two minutes after stopping the flow, the histogram had shifted to a 26% lower value and had changed its width at the base to 30%. In the next minute a significant change occurred in the degree of heterogeneity of the organ, and the width of the histogram had changed and its amplitude had increased 47% with respect to the previous histogram. These results can be interpreted to indicate that the liver acquired a bimodal distribution of signal, one of which was of low intensity (i.e., highly reduced) with a small population of signals more oxidized. This suggests that the anaerobic metabolism in the perfused liver is more heterogeneous than the aerobic metabolism, a point which is emphasized by previous data.

Figure 5B:
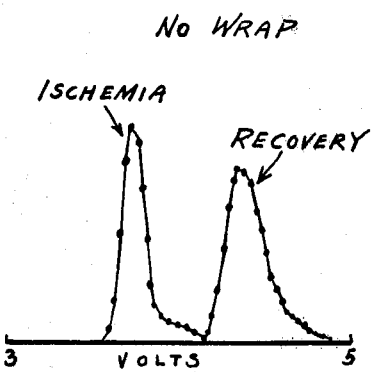

In perfused and intact organs it is possible to show the effect of oxygen diffusion from the air, for example in the rat brain. Similarly, exposure of the liver to air gives a distinctive heterogeneity of redox states, as shown in FIG. 5B. This Figure is on an expanded scale with 3 volts offset so that only 2 of the 5 volts of signal are displayed. In the normoxic-anoxic histograms a small number of signals (14% of the total area of the histogram) remains more oxidized. On recovery and reoxygenation, the same asymmetry remains, suggesting incomplete oxygenation of some of the liver cells. The diagram indicates the extreme sensitivity of the histogram method in indentifying heterogeneous redox states.

Figure 6A:
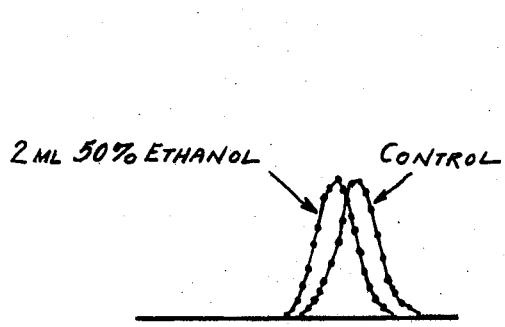
FIGS. 6A and 6B illustrate enlarged histogram displays obtained from the apparatus of FIG. 1 of flavoprotein signals from live rat liver tissue in situ as in FIGS. 5A and 5B, showing conditions (FIG. 6A) caused by administration of ethanol, and conditions of shift (FIG. 6B) from normoxia to hypoxia.

Flavoprotein fluorescence signals are effected by changes of blood flow and blood volume to a somewhat larger extent than in the case of reduced pyridine nucleotide. Histograms corresponding to normoxic-hypoxic changes and to metabolic shifts of the in situ liver of the anesthetized rat are recorded in FIGS. 6A and 6B. The animal was prepared with cannulation of the femoral vein for ethanol injection and cannulation of the trachea for control of the inspired gases. FIG. 6A shows the effect of a single administration of 2.0 ml of 50% ethanol by means of a stomach tube. The histogram was monitored for 30 min. after ethanol administration during which the ethanol was absorbed and distributed in the body tissues, resulting in a 10% shift of the histogram of the redox liver in situ. The heterogeneity of the liver metabolism was not altered at this concentration of infused ethanol.

Figure 6B:
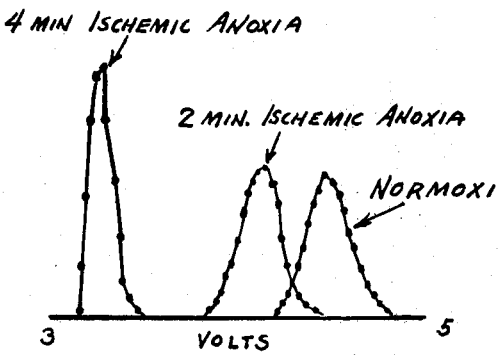

The shift from normoxia to hypoxia is indicated in FIG. 6B. The normoxic histogram is displayed on a magnified scale so that the left edge of the histogram corresponds to 3 volts of signal and the right edge to 5 volts. The initial effect of hypoxia is evidenced by a shift of the histogram to an intermediate position substantially without change of shape. As in the Saran-covered perfused organ, after 4 min. hypoxia, an increased homogeneity of the redox states is indicated by the 60% increase of height of the histogram and a corresponding narrowing of the peak. In summary, the histogram display of flavoprotein fluorescence from the in situ liver gives clear indications of metabolic and ischemic changes of redox state.

The flying spot technique is well suited for the evaluation of a wide range of conditions involving the heterogeneity of oxygen delivery to perfused or in situ organs. For example, it may be employed for the evaluation of size of a model cardiac infarct produced by occlusion of a branch of the coronary artery, or the like. The area scanned would then include the area of the infarct and a roughly equal volume of normal tissue, so that a bimodal histogram is obtained. The flying spot technique can also be effectively used for brain tissue, for example, for the NADH fluorometry of exposed cortex of an animal to determine required corrections for vasomotor changes which occur during systemic anoxia and sometimes local ischemia.

The above-described technique generally solves the problem of indentification of clear-cut metabolic heterogeneity and delineation of the nature and degree of such metabolic heterogeneity in organs prior to freeze-trapping, or in any case can be used for the evaluation of the localized metabolic state of particular areas in an organ. Flying spot two-dimensional representation, together with the "on-line" histogram affords a simple and near-optimal solution of this problem. One of the great advantages of the herein-described system is that the histograms may be acquired in a time short as compared to the time between metabolic transitions.

The flying spot technique can be used for a variety of other applications, with appropriate other wavelengths, both in fluorometry and reflectance spectroscopy. The technique may be used by the analytical chemist as a quick and effective way of deciding when it is important to carry out an extensive and exhaustive total, or more significantly, localized biochemical assay. The on-line display of the histogram allows the following of each second of metabolic transitions with appropriate substrates or inhibitors in normal or pathological states. At a time when the histogram may show maximal deviation from the normal histogram (and four such histograms can easily be stored in a typical apparatus according to the present invention) freeze-trapping of the organ is warranted and the biochemical data should show the most interesting deviation from normal states. Thus the ability to detect "maximal deviation" metabolic states may be of great use and assistance to the analytical biochemist.

While a specific embodiment of an improved flying spot fluorometer system has been disclosed in the foregoing description, it will be understood that various modifications within the spirit of the invention may occur to those skilled in the art. Therefore it is intended that no limitations be placed on the invention except as defined by the scope of the appended claims.

What is claimed is:

1. A method of fluorometrically measuring the metabolic condition of an area of animal tissue comprising irradiating the area with a spot of excitation radiation, deflecting the spot to form a repeated geometric scanning raster pattern on the area and causing emission of radiation from points on which the spot of excitation radiation is incident whose intensity is in accordance with the metabolic state of such points, generating respective electrical signals whose amplitudes are in accordance with the intensities of radiation emitted from said points, and forming a display from said signals synchronized with said raster pattern and showing the relative intensities of the radiation from said points.

2. The method of claim 1, and wherein the excitation radiation comprises a laser beam.

3. The method of claim 1, and generating reflectance-compensating electrical signals whose amplitudes are in accordance with the intensities of excitation radiation reflected from said points, subtracting the reflectance signals from said first-named electrical signals, and forming said display from the resultant difference signals.

4. The method of claim 1, and wherein said display-forming step includes forming an intensity-modulated cathode ray raster pattern synchronized with the excitation radiation raster pattern.

5. The method of claim 1, and wherein said display-forming step includes forming a histogram of the fluorescence signal intensity versus the frequency of occurrence of the various emission signal intensities within limited ranges over the total range of intensities.

6. The method of claim 1, and wherein the excitation radiation comprises the beam of an He-Cd laser, for exciting fluorescence in oxidized flavoprotein in said area of tissue.

7. The method of claim 1, and wherein the excitation radiation comprises the beam of an Argon ion laser, for exciting fluorescence either in oxidized flavoprotein or reduced pyridine nucleotide in said area of tissue.

8. The method of claim 1, and wherein the spot is deflected so as to form a repeated substantially rectangular raster pattern.

9. A fluorometer apparatus for measuring the metabolic state of an area of animal tissue comprising a source of excitation radiation, means to direct said radiation from said source in the form of a beam to said area, means to deflect the beam to provide a repeated flying spot raster pattern on said area, whereby to generate emission radiation from the respective illuminated spots of the area of intensities in accordance with their metabolic state, photoelectric sensing means, means to direct the emission radiation to said sensing means, whereby to generate electrical signals in accordance with the emission intensities of the illuminated spots, and means to form an output on-line histogram display from said electrical signals indicating the relative intensities of the radiation emitted from said respective illuminated spots.

10. The fluorometer apparatus of claim 9, and wherein said display-forming means includes means to generate a visible raster pattern, means to synchronize said last-named raster pattern with the flying spot raster pattern applied to said area, and means to intensity-modulate the last-named raster pattern with said electrical signals.

11. The fluorometer apparatus of claim 9, and second photoelectric sensing means, means to divert a portion of the emission radiation to said second sensing means, filter means in the path of said diverted portion excluding fluorescence radiation from said diverted radiation portion, whereby said second sensing means receives substantially only reflected excitation radiation and whereby said second sensing means generates electrical signals in accordance with said reflected radiation, means to subtract said second-named electrical signals from the first-named electrical signals, and means to form said output display from the resultant difference signals.

12. The fluorometer apparatus of claim 9, and wherein said source of excitation radiation comprises a laser.

13. The fluorometer apparatus of claim 9, and wherein said display-forming means includes means to form a histogram synchronized with said raster pattern and indicating the frequency of occurrence of various signal intensities within limited ranges of intensities as a function of signal intensity.

14. The fluorometer apparatus of claim 9, wherein the source of excitation radiation comprises an He-Cd laser.

15. The fluorometer apparatus of claim 9, and wherein the source of excitation radiation comprises an Argon ion laser.

16. The fluorometer apparatus of claim 9, and wherein said deflecting means comprises respective spaced X-scan and Y-scan vibratory mirrors located in the directed path of radiation from said source, and means to drive said mirrors.

17. The fluorometer apparatus of claim 16, and means to synchronize said output display with the vibration of said Y-scan mirror.

18. The fluorometer apparatus of claim 16, and second photoelectric sensing means, a beam splitter in the optical path from said area to said first-named photoelectric sensing means arranged to divert a portion of the radiation from said area to said second sensing means, filter means between the beam splitter and the second sensing means passing substantially only excitation radiation reflected from said area, whereby said second photoelectric sensing means receives only said reflected excitation radiation from said area and generates electrical signals in accordance therewith, means to subtract said reflected excitation electrical signals from the first-named electrical signals to derive difference signals, and means to form said output display from said difference signals.

* * * * *